United States Patent [19]
Dolfini et al.

[11] 4,029,669
[45] June 14, 1977

[54] 6-BENZALIMINO-6-ARYLTHIO PENICILLANIC ACIDS AND DERIVATIVES THEREOF

[75] Inventors: Joseph E. Dolfini; Ekkehard Bohme, both of Cincinnati, Ohio; William A. Slusarchyk, Belle Mead, N.J.

[73] Assignee: E. R. Squibb & Sons, Inc., Princeton, N.J.

[22] Filed: Apr. 9, 1976

[21] Appl. No.: 675,393

Related U.S. Application Data

[62] Division of Ser. No. 500,435, Aug. 26, 1974, Pat. No. 3,965,093, which is a division of Ser. No. 183,642, Sept. 24, 1971, Pat. No. 3,855,233.

[52] U.S. Cl. .................. 260/306.7 C; 260/239.1
[51] Int. Cl.² ...................................... C07D 499/02

[58] Field of Search ................ 260/306.7 C, 239.1

[56] References Cited
UNITED STATES PATENTS

| | | | |
|---|---|---|---|
| 3,843,641 | 10/1974 | Christensen et al. | 260/239.1 |
| 3,862,182 | 1/1975 | Johnston | 260/239.1 |
| 3,868,365 | 2/1975 | Dolfini et al. | 260/239.1 |

*Primary Examiner*—Gerald A. Schwartz
*Attorney, Agent, or Firm*—Lawrence S. Levinson; Merle J. Smith; Stephen B. Davis

[57] ABSTRACT

6-Amino and 6-benzalimino-6-arylthio penicillins are disclosed. These compounds are useful as intermediates in the preparation of 6-acylamino-6-arylthio penicillins.

2 Claims, No Drawings

6-BENZALIMINO-6-ARYLTHIO PENICILLANIC ACIDS AND DERIVATIVES THEREOF

This application is a division of Ser. No. 500,435 filed on Aug. 26, 1974, now U.S. Pat. No. 3,965,093, which in turn was a division of Ser. No. 183,642 filed on Sept. 24, 1971 and now U.S. Pat. No. 3,855,233.

SUMMARY OF INVENTION

This invention relates to 6-substituted-6-aminopenicillanic acid having the following Formula I:

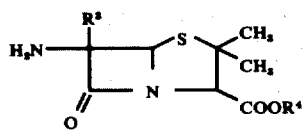

wherein $R^3$ is alkylsulfonyl, arylsulfonyl, aralkylsulfonyl, alkoxy, acyloxy, cyano, halogen, aralkoxy, acyl, arylthio, alkylthio, and alkyl having electronegative substituent therein such as halogen, cyano, perfluoro lower alkyl, substituted carbalkoxy, alkoxy, or aryloxy, etc. and $R^4$ is hydrogen, trialkylsilyl, lower alkyl, aralkyl, substituted alkyl, substituted aralkyl or cation. These compounds have been found to be useful as antibacterial agents and as intermediates in the preparation of 6-acylamino-6-substituted penicillanic acids and pharmaceutically acceptable salts thereof.

DESCRIPTION OF INVENTION

This invention relates to novel 6-substituted-6-amino penicillanic acid and derivatives thereof which are active as antibacterial agents and are valuable intermediates utilized in the preparation of the acylated derivatives. The 6-substituted-6-aminopenicillanic acids and salts of this invention also possess antibacterial activity which is enhanced by acylation of the 6-amino group. In Formula I above the term pharmaceutically acceptable cation means an alkali metal (e.g., sodium and potassium), an alkaline earth metal (e.g., calcium and magnesium), ammonium, or an amine, such as a lower alkyl amine (e.g., methylamine), a di(lower alkyl)amine (e.g., diethylamine), a phenyl-lower alkylamine (e.g., benzylamine), a di(phenyl-lower alkyl)amine (e.g., dibenzylamine), or an alkylenediamine (e.g., N,N'-dibenzylethylenediamine), or the like.

Compounds of Formula I are prepared by reacting a Schiff's base of 6-aminopenicillanic acid of Formula II:

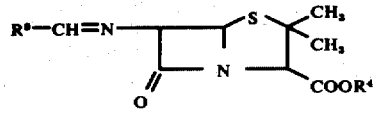

wherein $R^9$ is phenyl, X-substituted phenyl, lower alkyl or aralkyl (e.g., benzyl or phenethyl), wherein X is halogen (e.g., chloro, bromo), alkoxy, hydroxy, nitro, amine, or lower alkyl; with electrophilic reagent having the Formula III:

wherein L is leaving group such as halogen (e.g., chloro-, bromo-, and so forth), sulfonate, sulfate, methylsulfonyloxy, p-toluenesulfonyloxy, and $R^3$ is as defined herein.

This reaction is conducted in the presence of a base, such as alkali metal hydroxide such as sodium hydroxide, potassium t-butoxide or sodium methoxide, or sodium hydride.

Compounds of Formula III that may be utilized in the practice of the invention are perchloryl fluoride, trifluoromethyl iodide, cyanogen chloride, acetyl chloride, benzoyl chloride, ethyl chloroformate, methylsulfenyl chloride, phenylsulfenyl chloride, chlorine, ethyl chloroformate, methyl chloromethyl ether and so forth.

It is to be understood that the term lower alkyl and lower alkoxy in the formulae of the instant invention include straight and branched chain radicals of from 1 to about 8 carbons such as methyl, ethyl, propyl, isopropyl, butyl, isobutyl, t-butyl, amyl, methoxy, ethoxy, propoxy, isopropoxy, and the like. Further, it will be appreciated that certain of the compounds of this invention exist in different optically active forms. The various stereoisomeric forms as well as the racemic compounds are within the scope of this invention.

Suitable compounds of Formula II include any Schiff's base of 6-APA (or a protected form thereof). When using this process, the preferred Schiff's bases are those formed with aldehydes which do not interfere with the substitution reaction. Thus, although any of the Schiff's bases of 6-APA disclosed in U.S. Pat. No. 3,288,800 can be used, the preferred are those formed from aldehydes of the formula: RCHO, wherein R is phenyl, p-methoxyphenyl, m-nitrophenyl, halophenyl (e.g., p-chlorophenyl, m-fluorophenyl and o-bromophenyl), (lower alkoxy)phenyl (e.g., o-methoxyphenyl), carbo(lower alkoxy)phenyl (e.g., p-carbomethoxyphenyl, o-carboethoxyphenyl, p-carbohexyloxyphenyl, and m-carbobutoxyphenyl), o-n-propoxyphenyl, and p-n-hexyloxyphenyl), di(lower alkyl) aminophenyl [e.g., p-dimethylaminophenyl, o-diethylaminophenyl, o-diethylaminophenyl, p-(N-n-butyl-N-methylamino)-phenyl, and m-di-n-pentylaminophenyl], naphthyl. The reaction in forming compounds of Formula II is preferably conducted in an inert organic solvent for the Schiff's base reactant, such as methylene chloride, benzene, dimethoxyethane, dioxane and chloroform.

Compounds of the Formula II are preferably used in the form of an ester. Suitable esters include those formed with lower alkanols (e.g., methanol, ethanol and tert.-butanol), cycloalkanols (e.g., cyclohexanol and cyclopentanol), carbocyclic aryl alcohols (e.g. phenol and 2-naphthol), carbocyclic aryl (lower alkanols), e.g., (benzyl alcohol, p-methoxybenzyl alcohol benzhydrol, 1-naphthylmethyl alcohol and 2-phenylethanol), trimethylsilyl, lower alkanoyl (lower alkanols) (e.g., hydroxyacetone and pivaloylmethanol), carbocyclic aroyl(lower alkanols) (e.g., benzoylmethanol, 2-benzoylethanol and 2-naphthylcarbonylmethanol), cycloalkylcarbonyl(lower alkanols) (e.g., hydroxymethylcyclohexylketone), lower alkanoyloxy (lower alkanols) (e.g., pivaloyloxymethanol), and substituted derivatives of any of the above, such as lower alkyl (e.g., methyl and ethyl), lower alkoxy (e.g., methoxy and butoxy), halo (e.g., chloro, fluoro and bromo), and nitro derivatives, as exemplified by 2,2,2-trichloroethanol, 2-bromoethanol, p-nitrophenol, p-methoxyphenol, p-methoxybenzyl alcohol, p,p'-dimethoxybenzhydrol, 2-dimethylamino ethanol, p-nitrobenzoylmethanol and p-methoxybenzoylmethanol.

The reaction of Compound II with Compound III yields a compound of Formula IV:

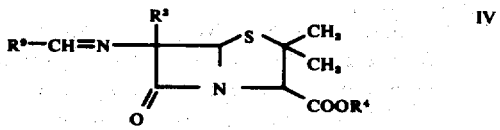

which can then be converted to compounds of Formula I by hydrolysis in the presence of a mild aqueous acid, such as hydrochloric, sulfuric, formic, p-toluenesulphonic acid, trifluoroacetic and acetic acid to yield the 6-substituted-6-aminopenicillanic acid of Formula I, preferably isolated as a salt.

As stated above compounds of Formula I are valuable intermediates in the formation of acylated compounds having the Formula V:

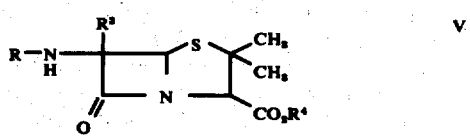

wherein $R^3$ and $R^4$ are as defined herein and R is acyl. Acyl in this invention is defined as:

a. $R^2(CH_2)_nCO$—where $R^2$ is phenyl, nitrophenyl, chlorophenyl, bromophenyl, lower alkyl phenyl, lower alkoxy phenyl, cycloalkyl or thienyl, and n is an integer from 0, 1 to 4, b. $R^5CO$—where $R^5$ contains from 2 to 7 carbon atoms and is alkyl, alkylthioalkyl or alkoxyalkoxyalkyl, c. $R^6CO$—where $R^6$ contains from 2 to 7 carbon atoms and is alkenyl, alkylthioalkenyl, alkenylthioalkyl, alkoxyalkenyl or alkenyloxyalkyl, d. $R^2X_1(CH_2)_nCO$—where $R^2$ and n are as defined above and $X_1$ is oxygen or sulphur.

e. $R^2(CH_2)_nS(CH_2)_mCH_2CO$—where $R^2$ and n are as defined above and m is 0 or an integer from 1 to 4.

f. $R^2CO$—where $R^2$ is as defined above, g. $R_7(CH_2)_nCO$—where $R^7$ is heterocyclic or substituted heterocyclic (e.g., lower alkyl dihydrocyclohexyl, lower alkoxy dihydrocyclohexyl such as 2,4-dimethyl-2,4-dihydrocyclohexyl, and 2-propoxy-2,4-dihydrocyclohexyl) and n is an integer from 0, 1 to 4, h.

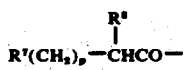

where $R^7$ is as defined herein, $R^8$ is amino, ureido, carboxy, sulfonyl, phosphonyl, hydrogen, hydroxy, chloro, bromo, or iodo, p is an integer from 0, 1 to 3, and

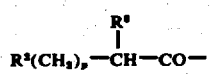

where $R^2$, $R^8$ and p are as defined above.

The formation of compounds of general Formula V may, for example, be effected by one of the following methods:

a. Reaction of the compound of general Formula I with an acid chloride, or acid anhydride, active ester, acid azide, etc. in aqueous or organic solution.

b. Reaction of the compound of general Formula I with a mixed anhydride of an acid corresponding to the desired acyl group and another acid, the mixed anhydride being formed by reaction of the acid corresponding to the desired acyl group with an alkyl haloformate, if desired formed in situ; the reaction with the mixed anhydride preferably being conducted in solution in an anhydrous, inert solvent in the presence of an acid binding agent e.g., a tertiary amine.

c. Reaction of the compound of Formula I with the activated form of a carboxylic acid formed by reaction with carbonyl-di-imidazole or dicyclohexylcarbodiimide or similar activating agent.

Acids, or functional derivatives thereof, which can be used to form derivatives of general Formula V include, in addition to the various acids corresponding to R, heterocyclic carboxylic acids e.g., nicotinic acid; substituted phosphorus acids e.g., dibenzylphosphorus acid; sulphonic acids (e.g., p-toluene sulphonic acid; and dicarboxylic acids.

The compounds of this invention have a broad spectrum of antibiotic activity. They have antibacterial activity against both gram-positive and gram-negative organisms, such as *Staphylococcus aureus*, *Salmonella schottmuelleri*, *Pseudomonas aeruginosa*, *Proteus vulgaris*, *Escherichia coli* and *Streptococcus pyrogenes*. They may be used as antibacterial agents in a prophylactic manner, e.g., in cleaning or disinfecting compositions, or otherwise to combat infections due to organisms such as those named above, and in general may be utilized in a manner similar to penicillin G and other penicillins. For example, a compound of Formula V may be used in various animal species in an amount of about 0.1 to 100 mg/kg daily, orally or parenterally, in single or two to four divided doses to treat infections of bacterial origin. Up to about 600 mg. of a compound of Formula V may be incorporated in an oral dosage form such as tablets, capsules, or elixirs or an injectable form in a sterile aqueous vehicle prepared according to conventional pharmaceutical factors. The compounds of this invention also have lower allergenicity as compared to non-6-substituted penicillins. In cleaning or disinfecting compositions, e.g., in farm or dairy equipment, a concentration of about 0.01 to 1% by weight of such compounds admixed with, suspended or dissolved in conventional inert dry or aqueous carriers by application by washing or spraying may be utilized.

The following examples illustrate the invention (all temperatures being in degrees Centigrade, unless otherwise stated):

EXAMPLE 1

N-Benzylidene-6-Aminopenicillanic Acid 73.8 Mmoles 6-aminopenicillanic acid, t-octylamine salt is added to 240 ml. methylene chloride cooled to 0°–5° C. (water bath). After dispersion 158.5 mmoles benzaldehyde are added, followed by the addition of an 8 ml. tetrahydrofuran solution containing 76.2 mmoles trifluoroacetic acid. During the course of this addition, the reaction mixture gradually clarifies to finally form a clear, slightly yellow solution. The reaction mixture is allowed to reach room temperature and concentrated to ⅛ its volume in vacuo at a temperature not exceeding 30° C. On cooling the desired product crystallized out in 82 mole %.

EXAMPLE 2

P-methoxy benzyl ester of N-benzylidene-6-aminopenicillanic acid a. Treatment of a 0.1 molar solution of N-benzylidene-6-aminopenicillanic acid with one equivalent of p-methoxy phenyl diazomethane in ether (Overberger and Anselme, J. ORG. CHEM., 28, 592 [1963]; Idem, J. AM. CHEM. SOC., 86, 658 [1964]) for one hour, followed by evaporation deposits the product.

(b) 0.1 equivalent N-salicilidene-6-aminopenicillanic acid in 400 ml dichloromethane is cooled to 3°–5° C and then treated with 0.1 equivalent pyridine and anisyl alcohol. This is followed by the addition of 0.1 equivalent dicylohexylcarbodiimide in dichloromethane over ½ hour. The reaction temperature is then maintained between 3°–5° C for ½ hour, at room temperature for ½ hour and between 35°–46° C for one (1) hour. After cooling in ice for 1 hour the formed urea is filtered off. The filtrate is washed twice with water, once at pH 3.5 then at pH 7.5. The organic layer is separated, dried over magnesium sulphate and evaporated to give, after crystallization 0.073 equivalent of N-salycilidene-6-aminopenicillanic acid, p-methoxy-benzyl ester. This is then treated with 1 equivalent p-toluenesulphonic acid and water in ethyl acetate for four hours. The formed p-toluenesulphonic acid salt of 6-aminopenicillanic acid, p-methoxy benzyl ester is then filtered off and treated with aqueous sodium bicarbonate to give 0.045 equivalent free amine. This is then treated with 0.045 equivalent benzaldehyde in benzene with a large excess of magnesium sulphate for four hours. The latter is removed by filtration and the filtrate is evaporated to give 0.042 equivalent pure desired product.

EXAMPLE 3

Diphenylmethyl ester of N-benzylidene-6-aminopenicillanic acid

Substitution of one equivalent of diphenyldiazomethane for the solution of phenyl diazomethane in Example 2(a) gives the desired product.

EXAMPLE 4

Trichloroethyl ester of 6-benzaliminopenicillanic acid

The Schiff base of Example 1 (10.0 g) is dissolved in 150 ml of dichloromethane containing pyridine (5.2 g). Trichloroethanol (9.84 g) is added followed by 6.79 g dicyclohexylcarbodiimide and the mixture stirred for 2 hours at room temperature. Precipitation of dicyclohexylurea occurs quickly. After 2 hours the precipitate is filtered off. The filtrate is diluted with dichloromethane and washed twice with an equal volume of water, first at pH 3.5, then at pH 7.2. It is then washed with saturated sodium chloride, dried over anhydrous magnesium sulfate, and stripped to dryness in vacuo. Wt. of yellow oil = 15.6 g.

The product is crystallized by dissolving it in 5 ml of ether and adding hexane to the warm solution until slightly turbid upon cooling.

EXAMPLE 5

Methyl ester of 6-benzaliminopenicillanic acid

By treating a dioxane solution of the product of Example 1 with excess ethereal diazomethane, followed by evaporation of the solvent, the desired product is obtained. Trituration with hexane gives a powder.

EXAMPLE 6

6-Benzalimino-6-cyanopenicillanic acid, p-methoxybenzyl ester

A solution of 100 mg. of 6-benzalimino-penicillanic acid, p-methoxybenxyl ester, in 5 ml. of dimethoxyethane was treated with 35 mg of potassium t-butoxide at −10° C under an argon atmosphere. After stirring for 5 minutes a solution of 20 mg of cyanogen chloride in 1 ml dimethoxy ethane was added. After stirring for 30 minutes the reaction mix was poured into pH 4.6 buffer and layered with ethyl acetate. The organic layer was washed with water and brine then dried ($Na_2SO_4$) and evaporated to deposit the product.

EXAMPLE 7

6-Benzalimino-6-ethoxycarbonyl penicillanic acid, p-methoxybenzyl ester

By following the procedure of Example 6, but substituting a solution of 78 mg of ethylchloroformate in 1 ml dimethoxy ethane in place of the ClCN the desired product is obtained.

EXAMPLE 8

6-Benzalimino-6-fluoropenicillanic acid, p-methoxybenzyl ester

By following the procedure of Example 6, but substituting 1 ml DME containing 38 mg of fluorylperchlorate for the ClCN solution, the desired product is obtained.

EXAMPLE 9

6-Benzalimino-6-p-nitrophenyl-thiopenicillanic acid, p-methoxybenzyl ester

A solution of 2.35 meq of 6-benzaliminopenicillanic acid, p-methoxybenzyl ester in 5 ml of dimethoxyethane was treated with 35 mg of potassium t-butoxide at −30° C under argon atmosphere. After 5 minutes 2.35 meq. of p-nitrophenylsulfenyl chloride is added and stirring continued for 15 minutes, the reaction mixture is diluted with pH 4.6 buffer and the suspension extracted with ethyl acetate. The organic extract is dried ($Na_2SO_4$) and evaporated at reduced pressure to deposit the product.

EXAMPLE 10

6-Benzalimino-6-acetylpenicillanic acid, p-methoxybenzyl ester.

12.5 Meq. 6-benzalimino-penicillanic acid, p-methoxybenzyl ester are dissolved in 2 ml. dry DME under nitrogen at −5° C. Then 12.5 meq. potassium t-butoxide is added. The reaction mixture turns yellow after a few minutes of stirring at that low temperature. Then a 20 fold excess acetyl chloride is added. After 3 hours, thin layer chromatography on silica gel, showed no more starting material. The reaction mixture is diluted with chloroform washed with water, dried over magnesium sulphate and evaporated in vacuo to give the product.

EXAMPLE 10A

6-Benzalimino-6-methylthiopenicillanic acid, p-methoxybenzyl ester.

A solution of 141 mg of 6-benzalimino-penicillanic acid, p-methoxybenzyl ester in 5 ml of dimethoxyethane was treated with 37 mg potassium t-butoxide at −30° C under nitrogen atmosphere. After stirring for three minutes, 27 mg methylsulfenyl chloride was added, and stirring was continued for two minutes. The reaction was poured into cold pH 4.6 buffer and layered with ethyl acetate. The organic layer was washed with water, dried ($Na_2SO_4$), and evaporated at reduced pressure to deposit the product.

EXAMPLE 11

6-Benzalimino-6-acetylpenicillanic acid, methyl ester

Substitution of 12.5 meq. of the methyl ester of 6-benzyliminopenicillanic acid in Example 10 for the p-methoxybenzyl ester leads to the desired product.

EXAMPLE 12

6-Benzalimino-6-acetylpenicillanic acid, benzhydryl ester

By substituting 12.5 meq. of the benzhydryl ester for the p-methoxybenzyl ester of Example 10, the desired product is obtained.

EXAMPLE 13

6-Amino-6-acetylpenicillanic acid, p-methoxybenzyl ester a. 5.1 Meq. 6-benzalimino-6-acetylpenicillanic acid, p-methoxybenzyl ester are hydrolyzed in a 50:50 mixture of acetone and 0.1 N aqueous hydrochloric acid for 10 minutes. The reaction mixture is then diluted with water and washed with chloroform. The acidic layer is then basified and extracted with chloroform. This latter chloroform layer is dried over magnesium sulphate and evaporated to dryness in vacuo to give 6-amino-6-acetylpenicillanic acid, p-methoxybenzyl ester.

b. 4.5 Meq. 6-benzalimino-6-acetylpenicillanic acid, p-methoxybenzyl ester are dissolved in ethyl acetate and treated with 5.5 meq. p-toluenesulphoric acid and water for 4 hours. The formed solid is removed by filtration and shaken between aqueous bicarbonate and dichloromethane. The organic layer is dried over magnesium sulphate and evaporated to dryness to give 2.7 meq. of the desired compound.

EXAMPLE 13A

6-Amino-6-methylthiopenicillanic acid, p-methoxybenzyl ester.

Substituting the product of Example 10A for the substrate in Example 13, and following the procedure therein, the desired product is obtained.

EXAMPLE 14

6-Amino-6-acetylpenicillanic acid, methyl ester

Substituting 5.1 meq of the product of Example 11 for the substrate of Example 13, and following the procedure therein, the desired product is obtained.

EXAMPLE 15

6-Amino-6-acetylpenicillanic acid, benzhydryl ester

Substituting 5.1 meq. of the product of Example 12 for the substrate of Example 13, and following the procedure therein, the desired product is obtained.

EXAMPLE 15A

6-Amino-6-acetyl penicillanic acid,

A solution of 100 mg of the 6-amino-6-acetyl penicillanic acid, p-methoxybenzyl ester in 15 ml water acidified to pH 2 by HCl is stirred at room temperature for 3 hours. The solution is extracted three times with 10 ml ether, then lyophilized to deposit the hydrochloride of the desired product.

EXAMPLE 16

6-Phenylacetamido-6-p-nitrophenyl thiopenicillanic acid, p-methoxybenzyl ester

A solution of 1.51 meq. of 6-benzalimino-6-p-nitrophenylsulfenyl penicillanic acid, p-methoxybenzyl ester in 10 ml. methyl isobutyl ketone is treated with 1.51 meq. of phenylacetyl chloride with ice bath cooling. One ml. of water and 1.51 meq. of triethylamine is then added. After 30 minutes the mixture is diluted with 50 ml. of ethyl acetate. The organic solution is washed with dilute aqueous bicarbonate solution followed by water and pH 4.6 buffer. It is dried ($Na_2SO_4$) and evaporated to give the product.

EXAMPLE 16A

6-Phenylacetamido-6-fluoropenicillanic acid, p-methoxybenzyl ester

By substituting product of Example 8 for 6-benzalimino-6-p-nitrophenylsulfenyl-penicillanic acid, p-methoxybenzyl ester in Example 16 the desired product was obtained.

EXAMPLE 17

6-Phenylacetamido-6-acetylpenicillanic acid, p-methyoxybenzyl ester 2.25 Meq. 6-amino-6-acetylpenicillanic acid, p-methoxybenzyl ester are dissolved in 30 ml. chloroform, and cooled to ice-bath temperature under nitrogen. Then 2.25 meq. triethylamine are added followed by the addition of 2.25 meq. phenylacetylchloride. The reaction is allowed to proceed for 2 hours at ice-bath temperatures and under nitrogen. The solution is diluted with chloroform, washed with an aqueous solution at pH 7.2, washed with water, dried over magnesium sulphate, and evaporated to dryness to give 1.1 meq. of 6-phenylacetamido-6-acetylpenicillanic acid, p-methoxybenzyl ester as a clear oil which crystallizes on standing.

EXAMPLE 17A

6-Phenylacetamido-6-methylthiopenicillanic acid, p-methoxybenzyl ester

1. By substituting the product of Example 10A for 6-benzalimino-6-p-nitrophenylsulfenylpenicillnic acid, p-methoxybenzyl ester in Example 16 the desired product was obtained.

2. By substituting the product of Example 13A for 6-amino-6-acetylpenicillanic acid, p-methoxybenzyl ester in Example 17, the desired product fell out.

EXAMPLE 18

6-Phenylacetamido-6-methoxycarbonylpenicillanic acid, p-methoxybenzyl ester

Substitution of 2.25 meq. 6-amino-6-methoxycarbonylpenicillanic acid, p-methoxybenzyl ester, (prepared by using methylchloroformate in place of the cyanogen chloride in Example 6 followed by hydrolysis, as in Example 13, for 6-amino-6-acetylpenicillanic acid, p-methoxybenzyl ester) in Example 17 yields the desired product.

EXAMPLE 19

6-Phenylacetamido-6-acetylpenicillanic acid a. 5 Grams 6-phenylacetamido-6-acetylpenicillanic acid, p-methoxybenzyl ester were dissolved in 25 ml dioxane; 5 ml. water. 10 grams 10% Pd/CaCO$_3$ are added and the mixture is treated with hydrogen until gas up-take ceases. The catalyst is then removed by filtration and the desired free acid is isolated in 69% yield.

b. By hydrolysis: A solution of 5 g. of the p-methoxybenzyl ester in 30 ml of 5:1 dioxane water is acidifed to pH2 with hydrochloric acid, after 1.5 hours, the solution is diluted with water, the pH adjusted to 7–8, and extracted with ether. The aqueous is then acidified and the product extorted into ether. The ether solution is washed (H$_2$O), dried (N$_a$SO$_4$) and evaporated to deposit the product.

EXAMPLE 20

6-Phenylacetamido-6-p-nitrophenylthiopenicillanic acid.

By substituting 6-phenylacetamido-6-p-nitrophenylsulfenylpenicillanic acid, p-methoxybenzyl ester for 6-phenylacetamido-6-acetylpenicillanic acid, p-methoxybenzyl ester in Example 19, the desired product is obtained.

EXAMPLE 21

6-Benzalimino-6-trifluoromethylpenicillanic acid, p-methoxybenzyl ester

6-Benzalimino-6-trifluoromethylpenicillanic acid, p-methoxybenzyl ester is prepared by using trifluoromethyl iodide in lieu of acetyl chloride of Example 10.

EXAMPLE 22

6-Amino-6-trifluoromethylpenicillanic acid, p-methoxy benzyl ester.

By substituting the product of Example 21 for 6-benzalimino-6-acetylpenicillanic acid, p-methoxybenzyl ester in Example 13, the desired product was formed.

EXAMPLE 22A

6-Phenylacetamido-6-trifluoromethylpenicillanic acid, p-methoxybenzyl ester.

By substituting product of Example 22 for 6-amino-6-acetylpenicillanic acid, p-methoxybenzyl ester in Example 13, the desired product was obtained.

EXAMPLE 22B

6-Phenylacetamido-6-fluoropenicillanic acid.

6-Phenylacetamido-6-fluoropenicillanic acid is prepared by Example 19, substituting the corresponding fluoro compound for the acetyl compound.

EXAMPLE 23

6-Amino-6-cyanopenicillanic acid, p-methoxybenzyl ester

6-Amino-6-cyanopenicillanic acid, p-methoxybenzyl ester is prepared by using the product of Example 6 to replace the substrate 6-acetyl compound of Example 13.

EXAMPLE 24

6-Phenylacetamido-6-cyanopenicillanic acid, p-methoxybenzyl ester

6-Phenylacetamido-6-cyanopenicillanic acid, p-methoxybenzyl ester is prepared by using the product of Example 23 for the substrate in Example 17.

EXAMPLE 25

6-Phenylacetamido-6-cyanopenicillanic acid

6-Phenylacetamido-6-cyanopenicillanic acid is prepared by the Example 19, substituting the corresponding cyano compound for the acetyl compound.

EXAMPLE 25A

6-Phenylacetamido-6-methoxycarbonylpenicillanic acid

6-Phenylacetamido-6-methoxycarbonylpenicillanic acid is prepared by Example 19, substituting the corresponding methoxycarbonyl compound for the acetyl compound.

EXAMPLE 25B

6-Phenylacetamido-6-methylthiopenicillanic acid

6-Phenylacetamido-6-methylthiopenicillanic acid is prepared by Example 19, substituting the corresponding methylthio compound for the acetyl compound.

EXAMPLES 26–48

6-Acylamino-6-acetylpenicillanic acids

By following the procedures of Example 17 and substituting an equivalent amount of the corresponding acid chloride of the following carboxylic acids α-(2-chlorophenoxy)propionic acid,
α-(4-sulfamylphenoxy)-n-butyric acid,
α-(3,4-dimethoxyphenoxy)-n-pentanoic acid,
α-(3-methylphenoxy)isovaleric acid,
α-(4-methylthiophenoxy)propionic acid,
α-(4-dimethylaminophenoxy)-n-hexanoic acid,
α-(2-methoxyphenoxy)-n-decanoic acid,
α-(2,4-dichlorophenoxy)phenylacetic acid,
α-(2-nitrophenoxy)-β-phenylpropionic acid,
α-(2-acetamidophenoxy)-γ-phenylbutyric acid,
α-(2,4-dimethylphenoxy)-n-butyric acid,
α-(4-isopropylphenoxy)propionic acid,
α-(3-bromophenoxy)-n-butyric acid,
α-(2-iodophenoxy)phenylacetic acid,
α-(2-diethylaminophenoxy)isovaleric acid,
α-(3,5-dichlorophenoxy)isohexanoic acid,
α-(4-cyclohexylphenoxy)propionic acid,
α-phenoxy-isovaleric acid,
α-phenoxy-n-decanoic acid,
α-phenoxy-γ-phenylbutyric acid,
α(2-benzylphenoxy)-n-butyric acid,
α-(2-trifluoromethylphenoxy)propionic acid, and
α-(4-fluorophenoxy)propionic acid, the products are obtained after following the procedure of Example 19,

- 6-[α-(2-chlorophenoxy)propionamido]-6-acetylpenicillanic acid,
- 6-[α-(4-sulfamylphenoxy)-n-butyramido]-6-acetylpenicillanic acid,
- 6-[α-(3,4-dimethoxyphenoxy)-n-pentanoamido]-6-acetylpenicillanic acid,
- 6-[α-(3-methylphenoxy)isovaleramido]-6-acetylpenicillanic acid,
- 6-[α-(4-methylthiophenoxy)propionamido]-6-acetylpenicillanic acid,
- 6-[α-(4-dimethylaminophenoxy)-n-hexanoamido]-6-acetylpenicillanic acid,
- 6-[α-(2-methoxyphenoxy)-n-decanoamido]-6-acetylpenicillanic acid,
- 6-[α-(2,4-dichlorophenoxy)phenylacetamido]-6-acetylpenicillanic acid,
- 6-[α-(2-nitrophenoxy)-β-phenylpropionamido]-6-acetylpenicillanic acid,
- 6-[α-(2-acetamidophenoxy)-γ-phenylbutyramido]-6-acetylpenicillanic acid,
- 6-[α-(2,4-dimethylphenoxy)-n-butyramido]-6-acetylpenicillanic acid,
- 6-[α-(4-isopropylphenoxy)propionamido]-6-acetylpenicillanic acid,
- 6-[α-(3-bromophenoxy)-n-butyramido]-6-acetylpenicillanic acid,
- 6-[α-(2-iodophenoxy)phenylacetamido]-6-acetylpenicillanic acid,
- 6-[α-(2-diethylaminophenoxy)isovaleramido]-6-acetylpenicillanic acid,
- 6-[α-(3,5-dichlorophenoxy)isohexanoamido]-6-acetylpenicillanic acid,
- 6-[α-(4-cyclohexylphenoxy)propionamido]-6-acetylpenicillanic acid,
- 6-[α-(phenoxy-isovaleramido]-6-acetylpencillanic acid,
- 6-[α-phenoxy-n-decanoamido]-6-acetylpenicillanic acid,
- 6-[α-phenoxy-2-phenylbutyramido]-6-acetylpenicillanic acid,
- 6-[α-(2-benzylphenoxy)-n-butyramido]-6-acetylpenicillanic acid,
- 6-[α-(2-trifluoromethylphenoxy)propionamido]-6-acetylpenicillanic acid, and
- 6-[α-(4-fluorophenoxy)propionamido]-6-acetylpenicillanic acid, respectively.

EXAMPLES 49–78

By following the procedure of Example 24 and substituting an equivalent amount of the corresponding acid chloride of the following carboxylic acids

- α-phenylthiopropionic acid,
- α-paranitrophenylthiopropionic acid,
- α-parachlorophenylthiopropionic acid,
- α-phenylthiobutyric acid,
- α-phenylthiocaproic acid,
- α-phenylthioisovaleric acid,
- α-(4-t-butylphenylthio)propionic acid,
- α-ortho-tolylthiopropionic acid,
- α-ortho-nitrophenylthiopropionic acid,
- α-parachlorophenylthiobutyric acid,
- α-(3,4,5-trichlorophenylthio)propionic acid,
- α-(3-trifluoromethylphenylthio)butyric acid,
- α-parabromophenylthioisovaleric acid,
- α-paraphenylphenylthiopropionic acid,
- α-(4-methoxyphenylthio)caproic acid,
- α-(4-cyclohexylphenylthio)butyric acid,
- α-phenylthio-α-cyclohexylacetic acid,
- α-phenylthio-α-cyclopentylacetic acid,
- α-(2,4-dichlorophenylthio)caproic acid,
- α-(2,4-diisoamylphenylthio)propionic acid,
- α-(4-benzylphenylthio)propionic acid,
- α-(4-sulfamylphenylthio)butyric acid,
- α-(2-allyloxyphenylthio)propionic acid,
- α-(4-allylphenylthio)isovaleric acid,
- α-(4-dimethylaminophenylthio)propionic acid,
- α-(2,5-dichlorophenylthio)butyric acid,
- α-(2-iodophenylthio)propionic acid,
- α-(2-acetamidophenylthio)propionic acid,
- α-(4-diethylaminophenylthio)propionic acid, and
- α-(3-fluorophenylthio)butyric acid, the products are obtained after following the procedure of Example 25,

- 6-(α-phenylthiopropionamido)-6-cyanopenicillanic acid,
- 6-(α-paranitrophenylthiopropionamido)-6-cyanopenicillanic acid,
- 6-(α-parachlorophenylthiopropionamido)-6-cyanopenicillanic acid,
- 6-(α-phenylthiobutyramido)-6-cyanopenicillanic acid,
- 6-(α-phenylthiocaproamido)-6-cyanopenicillanic acid,
- 6-(α-phenylthioisovaleramido)-6-cyanopenicillanic acid,
- 6-[α-(4-t-butylphenylthio)propionamido]-6-cyanopenicillanic acid,
- 6-[α-ortho-tolylthiopropionamido]-6-cyanopenicillanic acid,
- 6-(α-ortho-nitrophenylthiopropionamido)-6-cyanopenicillanic acid,
- 6-(α-parachlorophenylthiobutyramido)-6-cyanopenicillanic acid,
- 6-[α-(3,4,5-trichlorophenylthio)propionamido]-6-cyanopenicillanic acid,
- 6-[α-(3-trifluoromethylphenylthio)butyramido]-6-cyanopenicillanic acid,
- 6-(α-parabromophenylthioisovaleramido)-6-cyanopenicillanic acid,
- 6-(α-paraphenylphenylthiopropionamido)-6-cyanopenicillanic acid,
- 6-[α-(4-methoxyphenylthio)caproamido]-6-cyanopenicillanic acid,
- 6-[α-(4-cyclohexylphenylthio)butyramido]-6-cyanopenicillanic acid,
- 6-(α-phenylthio-α-cyclohexylacetamido)-6-cyanopenicillanic acid,
- 6-(α-phenylthio-α-cyclopentylacetamido)-6-cyanopenicillanic acid,
- 6-[α-(2,4-dichlorophenylthio)caproamido]-6-cyanopenicillanic acid,
- 6-[α-(2,4-diisoamylphenylthio)propionamido]-6-cyanopenicillanic acid,
- 6-[α-(4-benzylphenylthio)propionamido]-6-cyanopenicillanic acid,
- 6-[α-(4-sulfamylphenylthio)butyramido]-6-cyanopenicillanic acid,
- 6-[α-(2-allyloxyphenylthio)propionamido]-6-cyanopenicillanic acid,
- 6-[α-(4-allylphenylthio)isovaleramido]-6-cyanopenicillanic acid,
- 6-[α-(4-dimethylaminophenylthio)propionamido]-6-cyanopenicillanic acid, 6-[α-(2,5-dichlorophenylthio)butyramido]-6-cyanopenicillanic acid,
6-[α-(2-iodophenylthio)propionamido]-6-cyanopenicillanic acid,
6-[α-(2-acetamidophenylthio)propionamido]-6-cyanopenicillanic acid,
6-[α-(4-diethylaminophenylthio)propionamido]-6-cyanopenicillanic acid, and
6-[α-(3-fluorophenylthio)butyramido]-6-cyanopenicillanic acid, respectively.

EXAMPLES 79–92

By following the procedure of Example 16A and substituting an equivalent amount of the corresponding acid chloride of the following carboxylic acids
   D,L-α-amino-(3-thienyl)acetic acid,
   α-amino-5-ethyl-2-thienyl)acetic acid,
   α-amino-(5-methyl-2-thienyl)acetic acid,
   α-amino-(5-t-butyl-2-thienyl)acetic acid,
   α-amino-(2,5-dimethyl-3-thienyl)acetic acid,
   α-amino-(5-chloro-2-thienyl)acetic acid,
   α-amino-(5-bromo-2-thienyl)acetic acid,
   α-amino-(5-phenyl-3-chloro-2-thienyl)acetic acid,
   α-amino-3,5-dimethyl-2-thienyl)acetic acid,
   α-amino-(5-cyclohexyl-2-thienyl)acetic acid,
   α-amino-(5-diethylamino-2-thienyl)acetic acid,
   α-amino-(4-methylsulfonyl-2-thienyl)acetic acid,
   α-amino-(3-ethylthio-2-thienyl)acetic acid, and
   α-amino-(4-cycloheptyloxy-2-thienyl)acetic acid,
the products are obtained after following the procedure of Example 22,
   D,L-6-[α-amino-(3-thienyl)acetamido]-6-fluoropenicillanic acid,
   6-[α-amino-(5-ethyl-2-thienyl)acetamido]-6-fluoropenicillanic acid,
   6-[α-amino-(5-methyl-2-thienyl)acetamido]-6-fluoropenicillanic acid,
   6-[α-amino-(5-t-butyl)-2-thienyl)acetamido]-6-fluoropenicillanic acid,
   6-[α-amino-(2,5-dimethyl-3-thienyl)acetamido]-6-fluoropenicillanic acid,
   6-[α-amino-(5-chloro-2-thienyl)acetamido]-6-fluoropenicillanic acid,
   6-[α-amino-(5-bromo-2-thienyl)acetamido]-6-fluoropenicillanic acid,
   6-[α-amino-(5-phenyl-3-chloro-2-thienyl)acetamido]-6-fluoropenicillanic acid,
   6-[α-amino-(3,5-dimethyl-2-thienyl)acetamido]-6-fluoropenicillanic acid,
   6-[α-amino-(5-cyclohexyl-2-thienyl)acetamido]-6-fluoropenicillanic acid,
   6-[α-amino-(5-diethylamino-2-thienyl)acetamido]-6-fluoropenicillanic acid,
   6-[α-amino-(4-methylsulfonyl-2-thienyl)acetamido]-6-fluoropenicillanic acid,
   6-[α-amino-(3-ethylthio-2-thienyl)acetamido]-6-fluoropenicillanic acid, and
   6-[α-amino-(4-cycloheptyloxy-2-thienyl)acetamido]-6-fluoropenicillanic acid, respectively.

EXAMPLES 93–115

By following the procedure of Example 18 and substituting an equivalent amount of the corresponding acid chloride of the following carboxylic acids
   α-amino-p-chlorophenylacetic acid,
   α-amino-p-methoxyphenylacetic acid,
   L-(+)-α-aminophenylacetic acid,
   α-amino-4-diethylaminophenylacetic acid,
   α-amino-4-trifluoromethylphenylacetic acid,
   α-amino-2,4-dibromophenylacetic acid,
   α-amino-2-nitrophenylacetic acid,
   α-amino-3-methylphenylacetic acid,
   α-amino-4-sulfamylphenylacetic acid,
   α-amino-2-iodophenylacetic acid,
   α-amino-4-t-butylphenylacetic acid,
   α-amino-2-acetamidophenylacetic acid,
   α-amino-3-nitrophenylacetic acid,
   α-amino-3,4-dimethoxphenylacetic acid,
   α-amino-4-dimethylaminophenylacetic acid,
   α-amino-2,4-dichlorophenylacetic acid,
   α-amino-4-isopropylphenylacetic acid,
   α-amino-3-bromophenylacetic acid,
   α-amino-3-iodophenylacetic acid,
   α-amino-2-diethylaminophenylacetic acid,
   α-amino-2-trifluoromethylphenylacetic acid,
   α-amino-4-fluorophenylacetic acid, and
   α-amino-3,4,5-trifluoromethylphenylacetic acid,
the products are obtained by following the procedure of Example 25A are,
   6-(α-amino-p-chlorophenylacetamido)-6-methoxycarbonylpenicillanic acid,
   6-(α-amino-p-methoxyphenylacetamido)-6-methoxycarbonylpenicillanic acid,
   6-[L-(+)-α-aminophenylacetamido]-6-methoxycarbonylpenicillanic acid,
   6-(α-amino-4-diethylaminophenylacetamido)-6-methoxycarbonylpenicillanic acid,
   6-(α-amino-4-trifluoromethylphenylacetamido)-6-methoxycarbonylpenicillanic acid,
   6-(α-amino-2,4-dibromophenylacetamido)-6-methoxycarbonylpenicillanic acid,
   6-(α-amino-2-nitrophenylacetamido)-6-methoxycarbonylpenicillanic acid,
   6-(α-amino-3-methylphenylacetamido)-6-methoxycarbonylpenicillanic acid,
   6-(α-amino-4-sulfamylphenylacetamido)-6-methoxycarbonylpenicillanic acid,
   6-(α-amino-2-iodophenylacetamido)-6-methoxycarbonylpenicillanic acid,
   6-(α-amino-4-t-butylphenylacetamido)-6-methoxycarbonylpenicillanic acid,
   6-(α-amino-2-acetamidophenylacetamido)-6-methoxycarbonylpenicillanic acid,
   6-(α-amino-3-nitrophenylacetamido)-6-methoxycarbonylpenicillanic acid,
   6-(α-amino-3,4-dimethoxyphenylacetamido)-6-methoxycarbonylpenicillanic acid,
   6-(α-amino-4-dimethylaminophenylacetamido)-6-methoxycarbonylpenicillanic acid,
   6-(α-amino-2,4-dichlorophenylacetamido)-6-methoxycarbonylpenicillanic acid,
   6-(α-amino-4-isopropylphenylacetamido)-6-methoxycarbonylpenicillanic acid,
   6-(α-amino-3-bromphenylacetamido)-6-methoxycarbonylpenicillanic acid,
   6-(α-amino-3-iodophenylacetamido)-6-methoxycarbonylpenicillanic acid,
   6-(α-amino-2-diethylaminophenylacetamido)-6-methoxycarbonylpenicillanic acid,
   6-(α-amino-2-trifluoromethylphenylacetamido)-6-methoxycarbonylpenicillanic acid,
   6-(α-amino-4-fluorophenylacetamido)-6-methoxycarbonylpenicillanic acid,
   6-(α-amino-3,4,5-trifluoromethylphenylacetamido)-6-methoxycarbonylpenicillanic acid,

EXAMPLES 116–185

By following the procedure of Example 17 and substituting an equivalent amount of the following acid chloride of the 3,5-dinitrobenzoyl chloride,
2-chlorobenzoyl chloride,
2-methylbenzoyl chloride,
4-aminobenzoyl chloride,
4-nitrobenzoyl chloride,
4-hydroxybenzoyl chloride,
3,4,5-trimethoxybenzoyl chloride,
4-methylbenzoyl chloride,
4-chlorobenzoyl chloride,
3,4-dichlorobenzoyl chloride,
3-nitrobenzoyl chloride,
2,4,6-trimethoxybenzoyl chloride,
2-hydroxybenzoyl chloride,
4-ethoxybenzoyl chloride,
2,6-dimethoxybenzoyl chloride,
2,4,6-trimethylbenzoyl chloride,
2,6-dichlorobenzoyl chloride,
2,6-diethoxybenzoyl chloride,
2,6-di-n-butoxybenzoyl chloride,
2,6-dibenzyloxybenzoyl chloride,
2,3,6-trimethoxybenzoyl chloride,
2,4,6-tribromobenzoyl chloride,
2,6-di-n-propoxybenzoyl chloride,
2,6-dimethoxy-4-methylbenzoyl chloride,
4,6-diethyl-2-methoxybenzoyl chloride,
6-ethoxy-2-methoxybenzoyl chloride,
2-methylthiobenzoyl chloride,
2-benzylthiobenzoyl chloride,
2-phenoxybenzoyl chloride,
2-phenylbenzoyl chloride,
2-methoxybenzoyl chloride,
4-sulfamylbenzoyl chloride,
3,4-dimethoxybenzoyl chloride,
4-methoxybenzoyl chloride,
3-methylbenzoyl chloride,
3-dimethylaminobenzoyl chloride,
2-methoxybenzoyl chloride,
2-chloro-3,4,5-trimethoxybenzoyl chloride,
2,4-dichlorobenzoyl chloride,
2-nitrobenzoyl chloride,
4-methylaminobenzoyl chloride,
2-acetamidobenzoyl chloride,
2,4-dimethylbenzoyl chloride,
2,4,5-trimethylbenzoyl chloride,
4-isopropylbenzoyl chloride,
3-bromobenzoyl chloride,
2-iodobenzoyl chloride,
2-ethylaminobenzoyl chloride,
2,5-dihydroxybenzoyl chloride,
4-hydroxy-3-methoxybenzoyl chloride,
4-allylbenzoyl chloride,
4-allyloxybenzoyl chloride,
2-trifluoromethylbenzoyl chloride,
4-fluorobenzoyl chloride,
2-phenylthiobenzoyl chloride,
2-benzylbenzoyl chloride,
2,6-dihydroxybenzoyl chloride,
2,6-diacetoxybenzoyl chloride,
2,6-dimethylthiobenzoyl chloride,
2,4,6-trinitrobenzoyl chloride,
2,6-diacetamidobenzoyl chloride,
2,6-dibromobenzoyl chloride,
2,6-dimethylbenzoyl chloride,
2,6-diethylbenzoyl chloride,
2,6-diisopropylbenzoyl chloride,
2,6-diallyloxybenzoyl chloride,
3-bromo-2,6-dimethoxybenzoyl chloride,
4-chloro-2,6-dimethoxybenzoyl chloride,
2-chloro-6-nitrobenzoyl chloride, and
2-hydroxy-6-methoxybenzoyl chloride, the products obtained are, following the procedure of Example 19, 6-(3,5-dinitrobenzamido)-6-acetylpenicillanic acid,
6-(2-chlorobenzamido)-6-acetylpenicillanic acid,
6-(2-methylbenzamido)-6-acetylpenicillanic acid,
6-(4-aminobenzamido)-6-acetylpenicillanic acid,
6-(4-nitrobenzamido)-6-acetylpencillanic acid,
6-(4-hydroxybenzamido)-6-acetylpenicillanic acid,
6-(3,4,5-trimethoxybenzamido)-6-acetylpenicillanic acid,
6-(4-methylbenzamido)-6-acetylpenicillanic acid,
6-(4-chlorobenzamido)-6-acetylpenicillanic acid,
6-(3,4-dichlorobenzamido)-6-acetylpenicillanic acid,
6-(3-nitrobenzamido)-6-acetylpenicillanic acid,
6-(2,4,6-trimethoxybenzamido)-6-acetylpenicillanic acid,
6-(2-hydroxybenzamido)-6-methylpenicillanic acid,
6-(4-ethoxybenzamido)-6-acetylpenicillanic acid,
6-(2,6-dimethoxybenzamido)-6-acetylpenicillanic acid,
6-(2,4,6-trimethylbenzamido)-6-acetylpenicillanic acid,
6-(2,6-dichlorobenzamido)-6-acetylpenicillanic acid,
6-(2,6-diethoxybenzamido)-6-acetylpenicillanic acid,
6-(2,6-di-n-butoxybenzamido)-6-acetylpenicillanic acid,
6-(2,6-dibenzyloxybenzamido)-6-acetylpenicillanic acid,
6-(2,3,6-trimethoxybenzamido)-6-acetylpenicillanic acid,
6-(2,4,6-tribromobenzamido)-6-acetylpenicillanic acid,
6-(2,6-di-n-propoxybenzamido)-6-acetylpenicillanic acid,
6-(2,6-dimethoxy-4-methylbenzamido)-6-acetylpenicillanic acid,
6-(4,6-diethyl-2-methoxybenzamido)-6-acetylpenicillanic acid,
6-ethoxy-2-methoxybenzamido)-6-acetylpenicillanic acid,
6-(2-methylthiobenzamido)-6-acetylpenicillanic acid,
6-(2-benzylthiobenzamido)-6-acetylpenicillanic acid,
6-(2-phenoxybenzmido)-6-acetylpenicillanic acid,
6-(2-phenylbenzamido)-6-acetylpenicillanic acid,
6-(2-methoxybenzamido)-6-acetylpenicillanic acid,
6-(4-sulfamylbenzamido)-6-acetylpenicillanic acid,
6-(3,4-dimethoxybenzamido)-6-acetylpenicillanic acid,
6-(4-methoxybenzamido)-6-acetylpenicillanic acid,
6-(3-methylbenzamido)-6-acetylpenicillanic acid,
6-(3-dimethylaminobenzamido)-6-acetylpenicillanic acid,
6-(2-methoxybenzamido)-6-acetylpenicillanic acid,
6-(2-chloro-3,4,5-trimethoxybenzamido)-6-acetylpenicillanic acid, 6-(2,4-dichlorobenzamido)-6-acetylpenicillanic acid,
6-(2-nitrobenzamido)-6-acetylpenicillanic acid,
6-(4-methylaminobenzamido)-6-acetylpenicillanic acid,
6-(2-acetamidobenzamido)-6-acetylpenicillanic acid,
6-(2,4-dimethylbenzamido)-6-acetylpenicillanic acid,
6-(2,4,5-trimethylbenzamido)-6-acetylpenicillanic acid,
6-(4-isopropylbenzamido)-6-acetylpenicillanic acid,
6-(3-bromobenzamido)-6-acetylpenicillanic acid,
6-(2-iodobenzamido)-6-acetylpenicillanic acid,
6-(2-ethylaminobenzamido)-6-acetylpenicillanic acid,
6-(2,5-dihydroxybenzamido)-6-acetylpenicillanic acid,
6-(4-hydroxy-3-methoxybenzamido)-6-acetylpenicillanic acid,
6-(4-allylbenzamido)-6-acetylpenicillanic acid,
6-(4-allyloxybenzamido)-6-acetylpenicillanic acid,
6-(2-trifluoromethylbenzamido)-6-acetylpenicillanic acid,
6-(4-fluorobenzamido)-6-acetylpenicillanic acid,
6-(2-phenylthiobenzamido)-6-acetylpenicillanic acid,
6-(2-benzylbenzamido)-6-acetylpenicillanic acid,
6-(2,6-dihydroxybenzamido)-6-acetylpenicillanic acid,
6-(2,6-diacetoxybenzamido)-6-acetylpenicillanic acid,
6-(2,6-dimethylthiobenzamido)-6-acetylpenicillanic acid,
6-(2,4,6-trinitrobenzamido)-6-acetylpenicillanic acid,
6-(2,6-diacetamidobenzamido)-6-acetylpenicillanic acid,
6-(2,6-dibromobenzamido)-6-acetylpenicillanic acid,
6-(2,6-dimethylbenzamido)-6-acetylpenicillanic acid,
6-(2,6-diethylbenzamido)-6-acetylpenicillanic acid,
6-(2,6-diisopropylbenzamido)-6-acetylpenicillanic acid,
6-(2,6-diallyloxybenzamido)-6-acetylpenicillanic acid,
6-(3-bromo-2,6-dimethoxybenzamido)-6-acetylpenicillanic acid,
6-(4-chloro-2,6-dimethoxybenzamido)-6-acetylpenicillanic acid,
6-(2-chloro-6-nitrobenzamido)-6-acetylpenicillanic acid, and
6-(2-hydroxy-6-methoxybenzamido)-6-acetylpenicillanic acid, respectively.

EXAMPLES 186–196

By following the procedure of Example 16 and substituting an equivalent amount of the corresponding acid chloride of the following carboxylic acids
(4-nitrophenyl)acetyl chloride,
(4-bromophenyl)acetyl chloride,
(4-t-butylphenyl)acetyl chloride,
(4-trifluoromethylphenyl)acetyl chloride,
(3-fluorophenyl)acetyl chloride,
(4-sulfamylphenyl)acetyl chloride,
(2-benzylphenyl)acetyl chloride,
(3-methoxyphenyl)acetyl chloride,
(2-iodophenyl)acetyl chloride,
(3-diethylaminophenyl)acetyl chloride, and
(2,4-diisoamylphenyl)acetyl chloride, the products are obtained by following the procedure of Example 20:
6-[α-(4-nitrophenyl)acetamido]-6-nitrophenylthiopenicillanic acid,
6-[α-(4-bromophenyl)acetamido]-6-nitrophenylthiopenicillanic acid,
6-[α-(4-t-butylphenyl)acetamido]-6-nitrophenylthiopenicillanic acid,
6-[α-(4-trifluoromethylphenyl)acetamido]-6-nitrophenylthiopenicillanic acid,
6-[α-(3-fluorophenyl)acetamido]-6-nitrophenylthiopenicillanic acid,
6-[α-(4-sulfamylphenyl)acetamido]-6-nitrophenylthiopenicillanic acid, 6-[α-(2-benzylphenyl)acetamido]-6-nitrophenylthiopenicillanic acid,
6-[α-(3-methoxyphenyl)acetamido]-6-nitrophenylthiopenicillanic acid,
6-[α-(2-iodophenyl)acetamido]-6-nitrophenylthiopenicillanic acid,
6-[α-(3-diethylaminophenyl)acetamido]-6-nitrophenylthiopenicillanic acid, and
6-[α-(2,4-diisoamylphenyl)acetamido]-6-nitrophenylthiopenicillanic acid, respectively.

EXAMPLES 197–243

By following the procedure of Example 17A and substituting an equivalent amount of the following acid chloride
3-m-chlorophenyl-5-methyl-4-isoxazole-4-carbonyl chloride,
3-(3,4-dichlorophenyl)-5-methyl-4-isoxazole-4-carbonyl chloride,
3-p-tolyl-5-methyl-4-isoxazole-4-carbonyl chloride,
3-o-nitrophenyl-5-methyl-4-isoxazole-4-carbonyl chloride,
3-m-nitrophenyl-5-methyl-4-isoxazole-4-carbonyl chloride,
3-p-nitrophenyl-5-methyl-4-isoxazole-4-carbonyl chloride,
3-p-bromophenyl-5-methyl-4-isoxazole-4-carbonyl chloride,
3-p-fluorophenyl-5-methyl-4-isoxazole-4-carbonyl chloride,
3-p-methylsulfonylphenyl-5-methyl-4-isoxazole-4-carbonyl chloride,
3-p-methoxyphenyl-5-methyl-4-isoxazole-4-carbonyl chloride,
3-p-trifluoromethylphenyl-5-methyl-4-isoxazole-4-carbonyl chloride,
3-o-methoxyphenyl-5-methyl-4-isoxazole-4-carbonyl chloride,
3-p-ethoxyphenyl-5-methyl-4-isoxazole-4-carbonyl chloride,
3-(3,4-dimethoxyphenyl)-5-methyl-4-isoxazole-4-carbonyl chloride,
3-p-dimethylaminophenyl-5-methyl-4-isoxazole-4-carbonyl chloride,
3-α-naphthyl-5-methyl-4-isoxazole-4-carbonyl chloride,
3-β-naphthyl-4-methyl-4-isoxazole-4-carbonyl chloride,
3-phenyl-5-ethyl-4-isoxazole-4-carbonyl chloride,
3-p-chlorophenyl-5-ethyl-4-isoxazole-4-carbonyl chloride, 3-phenyl-5-isopropyl-4-isoxazole-4-carbonyl chloride,
3-phenyl-5-methylmercapto-4-isoxazole-4-carbonyl chloride,
3-methyl-5-o-chlorophenyl-4-isoxazole-4-carbonyl chloride,
3-methyl-5-p-bromophenyl-4-isoxazole-4-carbonyl chloride,
3-methyl-5-o-iodophenyl-4-isoxazole-4-carbonyl chloride,
3-methyl-5-(2,4-dichlorophenyl)-4-isoxazole-4-carbonyl chloride,
3-methyl-5-m-nitrophenyl-4-isoxazole-4-carbonyl chloride,
3-methyl-5-p-tolyl-4-isoxazole-4-carbonyl chloride,
3-methyl-5-p-nitrophenyl-4-isoxazole-4-carbonyl chloride,
3-methyl-5-p-methoxyphenyl-4-isoxazole-4-carbonyl chloride,
3-methyl-5-p-ethoxyphenyl-4-isoxazole-4-carbonyl chloride,
3-methyl-5-(2,6-dimethoxyphenyl)-4-isoxazole-4-carbonyl chloride,
3-methyl-5-p-methylsulfonylphenyl-4-isoxazole-4-carbonyl chloride,
3-methyl-5-p-fluorophenyl-4-isoxazole-4-carbonyl chloride,
3-methyl-5-p-cyanophenyl-4-isoxazole-4-carbonyl chloride,
3-methyl-5-p-methylmercaptophenyl-4-isoxazole-4-carbonyl chloride,
3-methyl-5-p-dimethylaminophenyl-4-isoxazole-4-carbonyl chloride,
3-methyl-5-α-naphthyl-4-isoxazole-4-carbonyl chloride,
3-methyl-5-β-naphthyl-4-isoxazole-4-carbonyl chloride,
3-ethyl-5-phenyl-4-isoxazole-4-carbonyl chloride,
3-ethyl-5-p-chlorophenyl-4-isoxazole-4-carbonyl chloride,
3-isopropyl-5-phenyl-4-isoxazole-4-carbonyl chloride,
3-tert. butyl-5-methyl-4-isoxazole-4-carbonyl chloride,
3-methyl-5-p-trifluoromethylphenyl-4-isoxazole-4-carbonyl chloride,
3-methyl-5-cyclohexyl-4-isoxazole-4-carbonyl chloride,
3-cyclohexyl-5-methyl-4-isoxazole-4-carbonyl chloride,
3-α-furyl-5-methyl-4-isoxazole-4-carbonyl chloride, and
3-α-thienyl-5-methyl-4-isoxazole-4-carbonyl chloride, the products obtained by following the procedures of Example 25B are
3-m-chlorophenyl-5-methyl-4-isoxazolyl-6-methylthiopenicillanic acid,
3-(3,4-dichlorophenyl)-5-methyl-4-isoxazolyl-6-methylthiopenicillanic acid,
3-p-tolyl-5-methyl-4-isoxazolyl-6-methylthiopenicillanic acid,
3-o-nitrophenyl-5-methyl-4-isoxazolyl-6-methylthiopenicillanic acid,
3-m-nitrophenyl-5-methyl-4-isoxazolyl-6-methylthiopenicillanic acid,
3-p-nitrophenyl-5-methyl-4-isoxazolyl-6-methylthiopenicillanic acid,
3-p-bromophenyl-5-methyl-4-isoxazolyl-6-methylthiopenicillanic acid,
3-p-fluorophenyl-5-methyl-4-isoxazolyl-6-methylthiopenicillanic acid,
3-p-methylsulfonylphenyl-5-methyl-4-isoxazolyl-6-methylthiopenicillanic acid,
3-p-methoxyphenyl-5-methyl-4-isoxazolyl-6-methylthiopenicillanic acid,
3-p-trifluoromethylphenyl-5-methyl-4-isoxazolyl-6-methylthiopenicillanic acid,
3-o-methoxyphenyl-5-methyl-4-isoxazolyl-6-methylthiopenicillanic acid,
3-p-ethoxyphenyl-5-methyl-4-isoxazolyl-6-methylthiopenicillanic acid,
3-(3,4-dimethoxyphenyl)-5-methyl-4-isoxazolyl-6-methylthiopenicillanic acid,
3-p-dimethylaminophenyl-5-methyl-4-isoxazolyl-6-methylthiopencillanic acid,
3-α-naphthyl-5-methyl-4-isoxazolyl-6-methylthiopenicillanic acid,
3-β-naphthyl-5-methyl-4-isoxazolyl-6-methylthiopenicillanic acid,
3-phenyl-5-ethyl-4-isoxazolyl-6-methylthiopenicillanic acid,
3-p-chlorophenyl-5-ethyl-4-isoxazolyl-6-methylthiopenicillanic acid,
3-phenyl-5-isopropyl-4-isoxazolyl-6-methylthiopenicillanic acid,
3-phenyl-5-methylmercapto-4-isoxazolyl-6-methylthiopenicillanic acid,
3-methyl-5-o-chlorophenyl-4-isoxazolyl-6-methylthiopenicillanic acid,
3-methyl-5-p-bromophenyl-4-isoxazolyl-6-methylthiopenicillanic acid,
3-methyl-5-o-iodophenyl-4-isoxazolyl-6-methylthiopenicillanic acid,
3-methyl-5-(2,4-dichlorophenyl)-4-isoxazolyl-6-methylthiopenicillanic acid,
3-methyl-5-m-nitrophenyl-4-isoxazolyl-6-methylthiopenicillanic acid,
3-methyl-5-p-tolyl-4-isoxazolyl-6-methylthiopenicillanic acid,
3-methyl-5-p-nitrophenyl-4-isoxazolyl-6-methylthiopenicillanic acid,
3-methyl-5-p-methoxyphenyl-4-isoxazolyl-6-methylthiopenicillanic acid,
3-methyl-5-p-ethoxyphenyl-4-isoxazolyl-6-methylthiopenicillanic acid,
3-methyl-5-(2,6-dimethoxyphenyl)-4-isoxazolyl-6-methylthiopenicillanic acid,
3-methyl-5-p-methylsulfonylphenyl-4-isoxazolyl-6-methylthiopenicillanic acid,
3-methyl-5-p-fluorophenyl-4-isoxazolyl-6-methylthiopenicillanic acid,
3-methyl-5-p-cyanophenyl-4-isoxazolyl-6-methylthiopenicillanic acid,
3-methyl-5-p-methylmercaptophenyl-4-isoxazolyl-6-methylthiopenicillanic acid,
3-methyl-5-p-dimethylaminophenyl-4-isoxazolyl-6-methylthiopenicillanic acid,
3-methyl-5-α-naphthyl-4-isoxazolyl-6-methylthiopenicillanic acid,
3-methyl-5-β-naphthyl-4-isoxazolyl-6-methylthiopenicillanic acid,
3-ethyl-5-phenyl-4-isoxazolyl-6-methylthiopenicillanic acid,
3-ethyl-5-p-chlorophenyl-4-isoxazolyl-6-methylthiopenicillanic acid, 3-isopropyl-5-phenyl-4-isoxazlyl-6-methylthiopenicillanic acid
3-tert. butyl-5-methyl-4-isoxazolyl-6-methylthiopenicillanic acid,
3-methyl-5-p-trifluoromethylphenyl-4-isoxazolyl-6-methylthiopenicillanic acid,
3-methyl-5-cyclohexyl-4-isoxazolyl-6-methylthiopenicillanic acid,
3-cyclohexyl-5-methyl-4-isoxazolyl-6-methylthiopenicillanic acid,
3-α-furyl-5-methyl-4-isoxazolyl-6-methylthiopenicillanic acid, and
3-α-thienyl-5-methyl-4-isoxazolyl-6-methylthiopenicillanic acid, respectively.

EXAMPLES 244–258

By following the procedure of Example 17A and substituting an equivalent amount of the following acid chloride
  3,5-diphenyl-4-isoxazole-4-carbonyl chloride,
  3-methyl-5-phenyl-4-isoxazole-4-carbonyl chloride,
  3,5-dimethyl-4-isoxazole-4-carbonyl chloride,
  5-benzyl-3-methyl-4-isoxazole-4-carbonyl chloride,
  3-methyl-5-styryl-4-isoxazole-4-carbonyl chloride,
  5-tert. butyl-3-phenyl-4-isoxazole-4-carbonyl chloride,
  5-(2-furyl)-3-methyl-4-isoxazole-4-carbonyl chloride,
  3-methyl-5-(3′,5′-dimethyl-4′-isoxazolyl)-4-isoxazole-4-carbonyl chloride,
  3-methyl-5-(2-thienyl)-4-isoxazole-4-carbonyl chloride,
  3-(p-chlorophenyl)-5-methyl-4-isoxazole-4-carbonyl chloride,
  3-methyl-5-methylmercapto-4-isoxazole-4-carbonyl chloride,
  5-(p-chlorophenyl)-3-methyl-4-isoxazole-4-carbonyl chloride,
  3-methyl-5-(o-nitrophenyl)-4-isoxazole-4-carbonyl chloride,
  5-isopropyl-3-methyl-4-isoxazole-4-carbonyl chloride, and
  5-methyl-3-(p-chlorophenyl)-4-isoxazole-4-carbonyl chloride,
the products obtained by following the procedures of Example 25B are
  3,5-diphenyl-4-isoxazolyl-6-methylthiopenicillanic acid,
  3-methyl-5-phenyl-4-isoxazolyl-6-methylthiopenicillanic acid,
  3,5-dimethyl-4-isoxazolyl-6-methylthiopenicillanic acid,
  5-benzyl-3-methyl-4-isoxazolyl-6-methylthiopenicillanic acid,
  3-methyl-5-styryl-4-isoxazolyl-6-methylthiopenicillanic acid,
  5-tert. butyl-3-phenyl-4-isoxazolyl-6-methylthiopenicillanic acid,
  5-(2-furyl)-3-methyl-4-isoxazolyl-6-methylthiopenicillanic acid,
  3-methyl-5-(3′,5′-dimethyl-4′-isoxazolyl)-4-isoxazolyl-6-methylthiopenicillanic acid,
  3-methyl-5-(2-thienyl)-4-isoxazolyl-6-methylthiopenicillanic acid,
  3-(p-chlorophenyl)-5-methyl-4-isoxazolyl-6-methylthiopenicillanic acid,
  3-methyl-5-methylmercapto-4-isoxazolyl-6-methylthiopenicillanic acid,
  5-(p-chlorophenyl)-3-methyl-4-isoxazolyl-6-methylthiopenicillanic acid,
  3-methyl-5-(o-nitrophenyl)-4-isoxazolyl-6-methylthiopenicillanic acid,
  5-isopropyl-3-methyl-4-isoxazolyl-6-methylthiopenicillanic acid,
  5-methyl-3-(p-chlorophenyl)-4-isoxazolyl-6-methylthiopenicillanic acid, respectively.

EXAMPLES 259–272

By following the procedure of Example 24 and substituting an equivalent amount of the following acid chloride
  α-(3-thienyl)gylcyl chloride,
  α-(5-ethyl-2-thienyl)glycyl chloride,
  α-(5-methyl-2-thienyl)glycyl chloride,
  α-(5-t-butyl-2-thienyl)glycyl chloride,
  α-(2,5-dimethyl-3-thienyl)glycyl chloride,
  α-(5-chloro-2-thienyl)glycyl chloride,
  α-(5-bromo-2-thienyl)glycyl chloride,
  α-(5-phenyl-3-chloro-2-thienyl)glycyl chloride,
  α-(3,5-dimethyl-2-thienyl)glycyl chloride,
  α-(5-cyclohexyl-2-thienyl)glycyl chloride,
  α-(5-diethylamino-2-thienyl)glycyl chloride,
  α-(4-methylsulfonyl-2-thienyl)glycyl chloride,
  α-(3-ethylthio-2-thienyl)glycyl chloride, and
  α-(4-cycloheptyloxy-2-thienyl)glycyl chloride, respectively.
the products obtained by following the procedure of Example 25 are
  D,L-6-[α-amino-(3-thienyl)acetamido]-6-cyanopenicillanic acid,
  6-[α-amino(5-ethyl-2-thienyl)acetamido]-6-cyanopenicillanic acid,
  6-[α-amino(5-methyl-2-thienyl)acetamido]-6-cyanopenicillanic acid,
  6-[α-amino(5-t-butyl-2-thienyl)acetamido]-6-cyanopenicillanic acid,
  6-[α-amino-2,5-dimethyl-3-thienyl)acetamido]-6-cyanopenicillanic acid,
  6-[α-amino-(5-chloro-2-thienyl)acetamido]-6-cyanopenicillanic acid,
  6-[α-amino-(5-bromo-2-thienyl)acetamido]-6-cyanopenicillanic acid,
  6-[α-amino-(5-phenyl-3-chloro-2-thienyl)acetamido]-6-cyanopenicillanic acid,
  6-[α-amino-(3,5-dimethyl-2-thienyl)acetamido]-6-cyanopenicillanic acid,
  6-[α-amino-(5-cyclohexyl-2-thienyl)acetamido]-6-cyanopenicillanic acid,
  6-[α-amino-(5-diethylamino-2-thienyl)acetamido]-6-cyanopenicillanic acid,
  6-[α-amino-(4-methylsulfonyl-2-thienyl)acetamido]-6-cyanopenicillanic acid,
  6-[α-amino-(3-ethylthio-2-thienyl)acetamido]-6-cyanopenicillanic acid, and
  6-[α-amino-(4-cycloheptyloxy-2-thienyl)acetamido]-6-cyanopenicillanic acid, respectively.

EXAMPLE 273

6-Amino-6-methoxymethyl penicillanic acid

A solution of 0.1 mole of N-benzylidene-6-amino penicillanic acid in 100 ml of dimethoxy ethane is treated with .05 mole of bic-trimethylsilyl acetamide at 0° C. After 30 minutes an equivalent of sodium hydride is added, followed 15 minutes later by 0.1 mole of methyl chloromethyl ether. After 1 hour the solution of 6-benzalimino-6-methoxymethylpenicillanic acid, trimethylsilyl ester is hydrolyzed by adding 100 ml water and adjusting to pH2. The solution is extracted with ethyl acetate and the pH readjusted to 4.5 to 5. Concentration of the aqueous deposits 6-amino-6-methoxymethylpenicillanic acid.

EXAMPLE 274

6-Amino-6-carboethoxymethylpenicillanic acid

By substituting 0.1 ml of ethyl bromoacetate for the methyl chloromethyl ether of the Example 273, the desired product is obtained.

EXAMPLE 275

6-(2-Thienylacetamido)-6-methoxymethylpenicillanic acid

A solution of 1 mmol of the product of Example 273 in 10 ml 1:1 aqueous acetone is treated with 1 mmol of 2-thienylacetyl chloride at 0° C. A solution of triethylamine in acetone is added to maintain a pH at 7.5. When no further pH change is noted, the reaction is extracted with ether. Acidification of the aqueous yields the desired free acid.

What is claimed is:

1. A compound of the formula

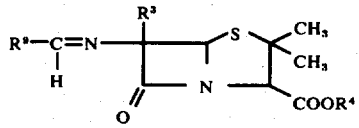

wherein $R^3$ is phenylthio or nitrophenylthio; $R^4$ is hydrogen, lower alkyl, benzyl, benzhydryl, methoxybenzyl, trimethylsilyl or trichloroethyl; and $R^9$ is phenyl or substituted phenyl wherein said substituent is selected from the group consisting of halogen, lower alkoxy, hydroxy, nitro, amino, and lower alkyl.

2. The compound of claim 1 wherein $R^3$ is p-nitrophenylthio, $R^4$ is p-methoxybenzyl; and $R^9$ is phenyl.

* * * * *